(12) United States Patent
Valencia et al.

(10) Patent No.: US 9,562,719 B2
(45) Date of Patent: Feb. 7, 2017

(54) METHOD OF REMOVING SOLIDS BY MODIFYING A LIQUID LEVEL IN A DISTILLATION TOWER

(71) Applicants: Jaime A. Valencia, Houston, TX (US); Paul Scott Northrop, Spring, TX (US)

(72) Inventors: Jaime A. Valencia, Houston, TX (US); Paul Scott Northrop, Spring, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 268 days.

(21) Appl. No.: 14/516,717

(22) Filed: Oct. 17, 2014

(65) Prior Publication Data

US 2015/0159945 A1 Jun. 11, 2015

Related U.S. Application Data

(60) Provisional application No. 61/912,983, filed on Dec. 6, 2013.

(51) Int. Cl.
*F25J 1/00* (2006.01)
*F25J 3/00* (2006.01)
(Continued)

(52) U.S. Cl.
CPC ............... *F25J 3/0266* (2013.01); *C07C 7/05* (2013.01); *C10L 3/104* (2013.01); *F25J 1/0022* (2013.01);
(Continued)

(58) Field of Classification Search
CPC ........ F25J 3/0209; F25J 3/0233; F25J 3/0266; F25J 2280/40; F25J 2205/20; F25J 3/061; F25J 3/0635; F25J 3/08; F25J 3/067; F25J 2200/02; F25J 2200/50; F25J 2200/74; F25J 2280/02; F25J 2280/20; Y02C 10/12; C10L 3/104; C10L 3/102
(Continued)

(56) References Cited

U.S. PATENT DOCUMENTS 2,621,216 A 12/1952 White ..................... 260/683.3
2,843,219 A 7/1958 Habgood .................. 183/114.2
(Continued)

FOREIGN PATENT DOCUMENTS

DE 3149847 7/1983 ............... B01D 5/00
EP 133208 2/1985 ............. B01D 53/14
(Continued)

OTHER PUBLICATIONS

Haut et al., "Development and Application of the Controlled Freeze Zone Process", (1988) SPE 17757, SPE Gas Tech. Symposium—Dallas, TX pp. 435-443.*

(Continued)

*Primary Examiner* — Keith Raymond
(74) *Attorney, Agent, or Firm* — ExxonMobil Upstream Research Company—Law Department

(57) ABSTRACT

The present disclosure provides a method of separating a feed stream in a distillation tower. The method includes maintaining a controlled freeze zone section in a distillation tower; maintaining a melt tray assembly within the controlled freeze zone section that operates at a temperature and pressure at which solid melts; forming solids in a controlled freeze zone section; raising a liquid level of a liquid in the melt tray assembly when the solids accumulate on a mechanical component in the controlled freeze zone section; raising a liquid temperature of the liquid while raising the liquid level; and lowering the liquid level after at least one of (a) a predetermined time period has passed and (b) an (Continued)

alternative temperature of the mechanical component is within an expected temperature range of a baseline temperature of the mechanical component.

18 Claims, 6 Drawing Sheets

(51) Int. Cl.
- *F25J 3/02* (2006.01)
- *F25J 3/06* (2006.01)
- *C10L 3/10* (2006.01)
- *C07C 7/05* (2006.01)
- *F25J 3/08* (2006.01)

(52) U.S. Cl.
CPC ............ *F25J 3/0209* (2013.01); *F25J 3/0233* (2013.01); *F25J 3/061* (2013.01); *F25J 3/067* (2013.01); *F25J 3/0635* (2013.01); *F25J 3/08* (2013.01); *C10L 3/102* (2013.01); *C10L 3/107* (2013.01); *C10L 2290/06* (2013.01); *C10L 2290/543* (2013.01); *C10L 2290/58* (2013.01); *C10L 2290/60* (2013.01); *F25J 2200/02* (2013.01); *F25J 2200/30* (2013.01); *F25J 2200/50* (2013.01); *F25J 2200/74* (2013.01); *F25J 2205/04* (2013.01); *F25J 2205/20* (2013.01); *F25J 2220/66* (2013.01); *F25J 2235/60* (2013.01); *F25J 2245/02* (2013.01); *F25J 2280/02* (2013.01); *F25J 2280/20* (2013.01); *F25J 2280/40* (2013.01); *F25J 2290/12* (2013.01); *Y02C 10/12* (2013.01)

(58) Field of Classification Search
USPC .................................................... 62/602, 929
See application file for complete search history.

(56) References Cited

U.S. PATENT DOCUMENTS

| | | | |
|---|---|---|---|
| 2,863,527 A | 12/1958 | Herbert | 183/115 |
| 2,960,837 A | 11/1960 | Swenson et al. | 62/24 |
| 3,050,950 A | 8/1962 | Karwat et al. | 62/13 |
| 3,109,726 A | 11/1963 | Karwat | 62/13 |
| 3,349,571 A | 10/1967 | Nebgen | 62/23 |
| 3,393,527 A | 7/1968 | Swensen et al. | 62/16 |
| 3,400,512 A | 9/1968 | McKay | 55/69 |
| 3,421,984 A | 1/1969 | Jensen et al. | 203/41 |
| 3,683,634 A | 8/1972 | Streich | 62/29 |
| 3,705,625 A | 12/1972 | Whitten et al. | 166/252 |
| 3,767,766 A | 10/1973 | Tjoa et al. | 423/220 |
| 3,824,080 A | 7/1974 | Smith et al. | 23/288 |
| 3,842,615 A | 10/1974 | Reigel et al. | 62/171 |
| 3,848,427 A | 11/1974 | Loofbourow | 62/260 |
| 3,895,101 A | 7/1975 | Tsuruta | 423/574 |
| 3,929,635 A | 12/1975 | Buriks et al. | 210/54 |
| 3,933,001 A | 1/1976 | Muska | 62/47 |
| 4,129,626 A | 12/1978 | Mellbom | 261/114 |
| 4,246,015 A | 1/1981 | Styring | 62/12 |
| 4,270,937 A | 6/1981 | Adler | 62/17 |
| 4,280,559 A | 7/1981 | Best | 166/303 |
| 4,281,518 A | 8/1981 | Muller et al. | 62/12 |
| 4,318,723 A | 3/1982 | Holmes et al. | 62/20 |
| 4,319,964 A | 3/1982 | Katz et al. | 202/172 |
| 4,336,233 A | 6/1982 | Appl et al. | 423/228 |
| 4,344,485 A | 8/1982 | Butler | 166/271 |
| 4,370,156 A | 1/1983 | Goddin et al. | 62/17 |
| 4,382,912 A | 5/1983 | Madgavkar et al. | 423/224 |
| 4,383,841 A | 5/1983 | Ryan et al. | 62/17 |
| 4,405,585 A | 9/1983 | Sartori et al. | 423/228 |
| 4,417,449 A | 11/1983 | Hegarty et al. | 62/28 |
| 4,417,909 A | 11/1983 | Weltmer | 62/12 |
| 4,421,535 A | 12/1983 | Mehra | 62/17 |
| 4,441,900 A | 4/1984 | Swallow | 62/29 |
| 4,459,142 A | 7/1984 | Goddin | 62/17 |
| 4,462,814 A | 7/1984 | Holmes et al. | 62/17 |
| 4,466,946 A | 8/1984 | Goddin et al. | 423/228 |
| 4,511,382 A | 4/1985 | Valencia et al. | 62/20 |
| 4,512,782 A | 4/1985 | Bauer et al. | 55/48 |
| 4,533,372 A * | 8/1985 | Valencia | F25J 3/0209 62/629 |
| 4,551,158 A | 11/1985 | Wagner et al. | 55/46 |
| 4,563,202 A | 1/1986 | Yao et al. | 62/17 |
| 4,592,766 A | 6/1986 | Kumman et al. | 62/18 |
| 4,602,477 A | 7/1986 | Lucadamo | 62/24 |
| 4,609,388 A | 9/1986 | Adler et al. | 62/12 |
| 4,636,334 A | 1/1987 | Skinner et al. | 252/377 |
| 4,695,672 A | 9/1987 | Bunting | 585/867 |
| 4,697,642 A | 10/1987 | Vogel | 166/263 |
| 4,710,213 A | 12/1987 | Sapper et al. | 62/28 |
| 4,717,408 A | 1/1988 | Hopewell | 62/20 |
| 4,720,294 A | 1/1988 | Lucadamo et al. | 62/31 |
| 4,747,858 A | 5/1988 | Gottier | 62/17 |
| 4,761,167 A | 8/1988 | Nicholas et al. | 62/17 |
| 4,762,543 A | 8/1988 | Pantermuehl et al. | 62/28 |
| 4,769,054 A | 9/1988 | Steigman | 62/12 |
| 4,822,393 A | 4/1989 | Markbreiter et al. | 62/17 |
| 4,831,206 A | 5/1989 | Zarchy | 585/737 |
| 4,923,493 A | 5/1990 | Valencia et al. | 62/13 |
| 4,927,498 A | 5/1990 | Rushmere | 162/168.3 |
| 4,935,043 A | 6/1990 | Blanc et al. | 62/20 |
| 4,954,220 A | 9/1990 | Rushmere | 162/168.3 |
| 4,972,676 A | 11/1990 | Sakai | 62/18 |
| 4,976,849 A | 12/1990 | Soldati | 208/351 |
| 5,011,521 A | 4/1991 | Gottier | 62/11 |
| 5,062,270 A | 11/1991 | Haut et al. | 62/12 |
| 5,120,338 A | 6/1992 | Potts et al. | 62/12 |
| 5,137,550 A | 8/1992 | Hegarty et al. | 55/43 |
| 5,152,927 A | 10/1992 | Rivers | 252/344 |
| 5,233,837 A | 8/1993 | Callahan | 62/38 |
| 5,240,472 A | 8/1993 | Sircar | 95/52 |
| 5,247,087 A | 9/1993 | Rivers | 544/357 |
| 5,265,428 A | 11/1993 | Valencia et al. | 62/36 |
| 5,335,504 A | 8/1994 | Durr et al. | 62/20 |
| 5,345,771 A | 9/1994 | Dinsmore | 62/18 |
| 5,567,396 A | 10/1996 | Perry et al. | 422/190 |
| 5,620,144 A | 4/1997 | Strock et al. | 239/557 |
| 5,643,460 A | 7/1997 | Marble et al. | 210/705 |
| 5,700,311 A | 12/1997 | Spencer | 95/236 |
| 5,720,929 A | 2/1998 | Minkkinen et al. | 422/190 |
| 5,819,555 A | 10/1998 | Engdahl | 62/637 |
| 5,820,837 A | 10/1998 | Marjanovich et al. | 423/220 |
| 5,899,274 A | 5/1999 | Frauenfeld et al. | 166/401 |
| 5,956,971 A | 9/1999 | Cole et al. | 62/623 |
| 5,964,985 A | 10/1999 | Wootten | 201/40 |
| 5,983,663 A | 11/1999 | Sterner | 62/620 |
| 6,053,007 A | 4/2000 | Victory et al. | 62/619 |
| 6,053,484 A | 4/2000 | Fan et al. | 261/114.1 |
| 6,082,133 A | 7/2000 | Barclay et al. | 62/619 |
| 6,082,373 A | 7/2000 | Sakurai et al. | 134/1 |
| 6,162,262 A | 12/2000 | Minkkinen et al. | 23/295 |
| 6,223,557 B1 | 5/2001 | Cole | 62/613 |
| 6,240,744 B1 | 6/2001 | Agrawal et al. | 62/643 |
| 6,267,358 B1 | 7/2001 | Gohara et al. | 261/110 |
| 6,270,557 B1 | 8/2001 | Millet et al. | 95/96 |
| 6,274,112 B1 | 8/2001 | Moffett et al. | 423/338 |
| 6,336,334 B1 | 1/2002 | Minkkinen et al. | 62/123 |
| 6,374,634 B2 | 4/2002 | Gallarda et al. | 62/620 |
| 6,401,486 B1 | 6/2002 | Lee et al. | 62/630 |
| 6,416,729 B1 | 7/2002 | DeBerry et al. | 423/573.1 |
| 6,442,969 B1 | 9/2002 | Rojey et al. | 62/618 |
| 6,500,982 B1 | 12/2002 | Hale et al. | 562/600 |
| 6,505,683 B2 | 1/2003 | Minkkinen et al. | 166/266 |
| 6,516,631 B1 | 2/2003 | Trebble | 62/630 |
| 6,517,801 B2 | 2/2003 | Watson et al. | 423/574.1 |
| 6,539,747 B2 | 4/2003 | Minta et al. | 62/620 |
| 6,565,629 B1 | 5/2003 | Hayashida et al. | 95/211 |
| 6,605,138 B2 | 8/2003 | Frondorf | 95/160 |
| 6,631,626 B1 | 10/2003 | Hahn | 62/612 |
| 6,632,266 B2 | 10/2003 | Thomas et al. | 95/49 |
| 6,662,872 B2 | 12/2003 | Gutek et al. | 166/272.4 |
| 6,708,759 B2 | 3/2004 | Leaute et al. | 166/272.4 |
| 6,711,914 B2 | 3/2004 | Lecomte | 62/625 |

(56) References Cited

U.S. PATENT DOCUMENTS

| | | | |
|---|---|---|---|
| 6,735,979 B2 | 5/2004 | Lecomte et al. | 62/611 |
| 6,755,251 B2 | 6/2004 | Thomas et al. | 166/265 |
| 6,755,965 B2 | 6/2004 | Pironti et al. | 208/347 |
| 6,818,194 B2 | 11/2004 | DeBerry et al. | 423/228 |
| 6,883,327 B2 | 4/2005 | Iijima et al. | 60/649 |
| 6,946,017 B2 | 9/2005 | Leppin et al. | 95/139 |
| 6,958,111 B2 | 10/2005 | Rust et al. | 202/158 |
| 6,962,061 B2 | 11/2005 | Wilding et al. | 62/613 |
| 7,001,490 B2 | 2/2006 | Wostbrock et al. | 203/1 |
| 7,004,985 B2 | 2/2006 | Wallace et al. | 48/198.3 |
| 7,066,986 B2 | 6/2006 | Haben et al. | 95/99 |
| 7,073,348 B2 | 7/2006 | Clodic et al. | 62/532 |
| 7,121,115 B2 | 10/2006 | Lemaire et al. | 62/625 |
| 7,128,150 B2 | 10/2006 | Thomas et al. | 166/266 |
| 7,128,276 B2 | 10/2006 | Nilsen et al. | 236/124 |
| 7,152,431 B2 | 12/2006 | Amin et al. | 62/637 |
| 7,211,128 B2 | 5/2007 | Thomas et al. | 95/135 |
| 7,211,701 B2 | 5/2007 | Muller et al. | 568/853 |
| 7,219,512 B1 | 5/2007 | Wilding et al. | 62/617 |
| 7,285,225 B2 | 10/2007 | Copeland et al. | 210/785 |
| 7,325,415 B2 | 2/2008 | Amin et al. | 62/541 |
| 7,424,808 B2 | 9/2008 | Mak | 62/625 |
| 7,437,889 B2 | 10/2008 | Roberts et al. | 62/619 |
| 7,442,231 B2 | 10/2008 | Landrum | 95/45 |
| 7,442,233 B2 | 10/2008 | Mitariten | 95/123 |
| 7,493,779 B2 | 2/2009 | Amin | 62/617 |
| 7,536,873 B2 | 5/2009 | Nohlen | 62/644 |
| 7,550,064 B2 | 6/2009 | Bassler et al. | 203/29 |
| 7,575,624 B2 | 8/2009 | Cartwright et al. | 95/51 |
| 7,597,746 B2 | 10/2009 | Mak et al. | 95/169 |
| 7,635,408 B2 | 12/2009 | Mak et al. | 95/187 |
| 7,637,984 B2 | 12/2009 | Adamopoulos | 95/45 |
| 7,637,987 B2 | 12/2009 | Mak | 95/160 |
| 7,641,717 B2 | 1/2010 | Gal | 95/187 |
| 7,662,215 B2 | 2/2010 | Sparling et al. | 95/172 |
| 7,691,239 B2 | 4/2010 | Kister et al. | 203/2 |
| 7,722,289 B2 | 5/2010 | Leone et al. | 405/53 |
| 7,729,976 B2 | 6/2010 | Hill et al. | 705/37 |
| 7,770,872 B2 | 8/2010 | Delatour | 261/110 |
| 7,795,483 B2 | 9/2010 | Kulprathipanja et al. | 585/24 |
| 7,806,965 B2 | 10/2010 | Stinson | 95/187 |
| 7,814,975 B2 | 10/2010 | Hagen et al. | 166/257 |
| 7,879,135 B2 | 2/2011 | Ravikumar et al. | 95/11 |
| 7,901,583 B2 | 3/2011 | McColl et al. | 210/710 |
| 7,955,496 B2 | 6/2011 | Iqbal et al. | 208/129 |
| 8,002,498 B2 | 8/2011 | Leone et al. | 405/53 |
| 8,020,408 B2 | 9/2011 | Howard et al. | 62/646 |
| 8,133,764 B2 | 3/2012 | Dirks et al. | 438/124 |
| 8,136,799 B2 | 3/2012 | Griepsma | 261/114.5 |
| 8,303,685 B2 | 11/2012 | Schubert et al. | 95/181 |
| 8,308,849 B2 | 11/2012 | Gal | 95/187 |
| 8,312,738 B2 | 11/2012 | Singh et al. | 62/629 |
| 8,372,169 B2 | 2/2013 | Tsangaris et al. | 48/120 |
| 8,381,544 B2 | 2/2013 | Coyle | 62/618 |
| 8,388,832 B2 | 3/2013 | Moffett et al. | 208/390 |
| 8,428,835 B2 | 4/2013 | Habert et al. | 701/54 |
| 8,475,572 B2 | 7/2013 | Prast et al. | 95/269 |
| 8,500,105 B2 | 8/2013 | Nieuwoudt | 261/79.2 |
| 8,529,662 B2 | 9/2013 | Kelley et al. | 95/96 |
| 2002/0174687 A1 | 11/2002 | Cai | 65/158 |
| 2002/0189443 A1 | 12/2002 | McGuire | 95/32 |
| 2003/0181772 A1 | 9/2003 | Meyer et al. | 585/324 |
| 2006/0207946 A1 | 9/2006 | McColl et al. | 210/733 |
| 2006/0239879 A1 | 10/2006 | Lallemand et al. | 423/210 |
| 2007/0056317 A1 | 3/2007 | Amin et al. | 62/532 |
| 2007/0144943 A1 | 6/2007 | Lemaire et al. | 208/208 |
| 2007/0277674 A1 | 12/2007 | Hirano et al. | 95/290 |
| 2008/0034789 A1 | 2/2008 | Fieler et al. | 62/623 |
| 2008/0091316 A1 | 4/2008 | Szczublewski | 701/36 |
| 2008/0092589 A1 | 4/2008 | Tranier et al. | 62/640 |
| 2008/0307827 A1 | 12/2008 | Hino et al. | 62/634 |
| 2009/0023605 A1 | 1/2009 | Lebl et al. | 506/27 |
| 2009/0220406 A1 | 9/2009 | Rahman | 423/437.1 |
| 2010/0011809 A1 | 1/2010 | Mak | 62/620 |
| 2010/0018248 A1* | 1/2010 | Fieler | F25J 3/0209 62/617 |
| 2010/0024472 A1 | 2/2010 | Amin et al. | 62/541 |
| 2010/0064725 A1 | 3/2010 | Chieng et al. | 62/620 |
| 2010/0107687 A1 | 5/2010 | Andrian et al. | 62/620 |
| 2010/0132405 A1 | 6/2010 | Nilsen | 62/611 |
| 2010/0147022 A1 | 6/2010 | Hart et al. | 62/601 |
| 2010/0187181 A1 | 7/2010 | Sortwell | 210/726 |
| 2010/0310439 A1 | 12/2010 | Brok et al. | 423/222 |
| 2011/0132034 A1 | 6/2011 | Beaumont et al. | 62/620 |
| 2011/0154856 A1 | 6/2011 | Andrian et al. | 62/618 |
| 2011/0168019 A1 | 7/2011 | Northrop et al. | 95/186 |
| 2011/0192190 A1 | 8/2011 | Andrian et al. | 62/617 |
| 2011/0265512 A1 | 11/2011 | Bearden et al. | 62/617 |
| 2012/0006055 A1 | 1/2012 | Van Santen et al. | 62/618 |
| 2012/0031143 A1 | 2/2012 | Van Santem et al. | 62/617 |
| 2012/0031144 A1 | 2/2012 | Northrop et al. | 62/617 |
| 2012/0079852 A1 | 4/2012 | Northrop et al. | 62/620 |
| 2012/0125043 A1 | 5/2012 | Cullinane et al. | 62/620 |
| 2012/0204599 A1 | 8/2012 | Northrop et al. | 62/617 |
| 2012/0279728 A1 | 11/2012 | Northrop et al. | 166/401 |
| 2013/0032029 A1 | 2/2013 | Mak | 95/94 |
| 2013/0074541 A1 | 3/2013 | Kaminsky et al. | 62/601 |
| 2013/0098105 A1 | 4/2013 | Northrop | 62/617 |
| 2014/0137599 A1 | 5/2014 | Oelfke et al. | 62/619 |

FOREIGN PATENT DOCUMENTS

| | | | |
|---|---|---|---|
| EP | 508244 | 10/1992 | B01D 53/34 |
| EP | 1338557 | 3/2005 | C01B 17/04 |
| GB | 1010403 | 11/1965 | |
| WO | WO 02/32536 | 4/2002 | B01F 13/00 |
| WO | WO 02/39038 | 5/2002 | F25J 3/06 |
| WO | WO 2004/047956 | 6/2004 | B01D 53/14 |
| WO | WO 2008/034789 | 3/2008 | G01K 11/00 |
| WO | WO 2008/095258 | 8/2008 | F25J 3/02 |
| WO | WO 2008/152030 | 12/2008 | B01D 53/00 |
| WO | WO 2009/023605 | 2/2009 | C10G 21/00 |
| WO | WO 2009/029353 | 3/2009 | E21B 43/00 |
| WO | WO 2009/087206 | 7/2009 | B01D 53/00 |
| WO | WO 2010/023238 | 3/2010 | F25J 3/06 |
| WO | WO 2010/052299 | 5/2010 | B01D 53/00 |
| WO | WO 2010/136442 | 12/2010 | B01D 53/00 |
| WO | WO 2011/026170 | 3/2011 | C10L 3/10 |
| WO | WO 2013/095828 | 6/2013 | B01D 53/00 |
| WO | WO 2013/142100 | 9/2013 | B03C 3/00 |

OTHER PUBLICATIONS

U.S. Appl. No. 14/516,686, filed Oct. 17, 2014, Valencia, J. A.
U.S. Appl. No. 14/516,689, filed Oct. 17, 2014, Cullinane, J. T. et al.
U.S. Appl. No. 14/516,705, filed Oct. 17, 2014, Valencia, J. A. et al.
U.S. Appl. No. 14/516,709, filed Oct. 17, 2014, Valencia, J. A.
U.S. Appl. No. 14/516,713, filed Oct. 17, 2014, Valencia, J. A. et al.
U.S. Appl. No. 14/516,717, filed Oct. 17, 2014, Valencia, J. A. et al.
U.S. Appl. No. 14/516,718, filed Oct. 17, 2014, Valencia, J. A.
U.S. Appl. No. 14/516,726, filed Oct. 17, 2014, Valencia, J. A. et al.
U.S. Appl. No. 14/516,731, filed Oct. 17, 2014, Valencia, J. A. et al.
Aaron, D. et al. (2005) "Separation of $CO_2$ from Flue Gas: A Review," *Separation Science and Technology,* 40, pp. 321-348.
Amin, R. (2003) "Advanced Mini Natural Gas Liquefier," *LNG Journal,* Mar.-Apr. 2003, pp. 20-23.
Black, S. (2006) "Chilled Ammonia Process for CO2 Capture," *Alstom Position Paper,* Nov. 2006, 6 pgs.
Ciulla, Vincent (2007) "How the Engine Works," *About.com,* Mar. 21, 2007, [retrieved from the internet on Aug. 17, 2012]. <URL: http://autorepair.about.com/cs/generalinfo/a/aa060500a.html>.
"Cryogenics" *Science Clarified,* May 2, 2006 [retrieved from the internet on Aug. 17, 2012]. <URL: http://www.scienceclarified.com/Co-Di/Cryogenics.html>.
Denton, R. D. et al. (1985) "Integrated Low Temperature Processing of Sour Natural Gas," *Gas Processors Assoc., 64th Ann. Conv.,* pp. 92-96.
Guccione, E. (1963) "New Approach to Recovery of Helium from Natural Gas," *Chem. Engr.,* Sep. 30, 1963, pp. 76-78.

(56) References Cited

OTHER PUBLICATIONS

Hassan, S. M. N. (2005) "Techno-Economic Study of $CO_2$ Capture Process for Cement Plants," *University of Waterloo—Thesis*.

Haut, R. C. et al. (1988) "Development and Application of the Controlled Freeze Zone Process," *SPE 17757, SPE Gas Tech. Symp.*—Dallas, TX, pp. 435-443.

Haut, R. C. et al. (1988) "Development and Application of the Controlled Freeze Zone Process," *OSEA 88197, 7th Offshore So. East Asia Conf.*, Singapore, Feb. 1988, pp. 840-848.

Haut, R. C. et al. (1989) "Development and Application of the Controlled Freeze Zone Process," *SPE Production Engineering*, Aug. 1989, pp. 265-271.

Im, U. K. et al. (1971) "Heterogeneous Phase Behavior of Carbon Dioxide in *n*-Hexane and *n*-Heptane at Low Temperatures," *Jrnl. of Chem. Engineering Data*, v.16.4, pp. 412-415.

Mitariten, M. et al. (2007) "The Sorbead™ Quick-Cycle Process for Simultaneous Removal of Water, Heavy Hydrocarbons and Mercaptans from Natural Gas," *Laurance Reid Gas Conditioning Conf.*, Feb. 25-27, 2007.

Northrop, P. Scott et al. (2004) "Cryogenic Sour Gas Process Attractive for Acid Gas Injection Applications," *83rd Ann. Gas Processors Assoc. Convention*, New Orleans, LA., pp. 1-8 (XP007912217).

Pagcatipunan, C. et al. (2005) "Maximize the Performance of Spray Nozzle Systems," *CEP Magazine*, Dec. 2005, pp. 38-44.

Reyes, S. C. et al. (1997) "Frequency Modulation Methods for Diffusion and Adsorption Measurements in Porous Solids," *J. Phys. Chem. B*, v.101, pp. 614-622.

Rubin, E. S. et al. (2002) "A Technical, Economic and Environmental Assessment of Amine-based CO2 Capture Technology for Power Plant Greenhouse Gas Control," *U.S. Dept. of Energy*, Oct. 2002, DOE/DE-FC26-00NT40935, 26 pages.

Spero, C. (2007) "Callide Oxyfuel Project," *CS Energy, cLET Seminar*, Jul. 12, 2007, 9 pages.

Thomas, E. R. et al. (1987) "Conceptual Studies Using the Controlled Freeze Zone (CFZ) Process," *AIChE Summer Nat'l Mtg.*, Aug. 16-19, 1987.

Thomas, E. R. et al. (1988) "Conceptual Studies for $CO_2$/Natural Gas Separation Using the Control Freeze Zone (CFZ) Process," *Gas Separation and Purification*, v. 2, pp. 84-89.

Valencia, J. A. et al. (2008) "Controlled Freeze Zone™ Technology for Enabling Processing of High $CO_2$ and $H_2S$ Gas Reserves," SPE-IPTC 12708, Kuala Lumpur, IN, v.4.1, Jan. 2008, pp. 2358-2363.

Victory, D. J. et al. (1987) "The CFZ Process: Direct Methane-Carbon Dioxide Fractionation," *66th Ann. GPA Convention*, Mar. 16-18, Denver, CO.

Wilson, R.W. et al. (1968) "Helium: Its Extraction and Purification," *Journ. Petrol. Tech.*, v. 20, pp. 341-344.

\* cited by examiner

METHOD OF REMOVING SOLIDS BY MODIFYING A LIQUID LEVEL IN A DISTILLATION TOWER

CROSS REFERENCE TO RELATED APPLICATIONS

This application claims the priority benefit of both U.S. Provisional patent application No. 61/912,983 filed Dec. 6, 2013 entitled METHOD OF REMOVING SOLIDS BY MODIFYING A LIQUID LEVEL IN A DISTILLATION TOWER, the entirety of which is incorporated by reference herein.

This application is related to but does not claim priority to U.S. Provisional patent application Nos.: 61/912,957 filed on Dec. 6, 2013 entitled METHOD AND DEVICE FOR SEPARATING HYDROCARBONS AND CONTAMINANTS WITH A SPRAY ASSEMBLY; 62/044,770 filed on Sep. 2, 2014 entitled METHOD AND DEVICE FOR SEPARATING HYDROCARBONS AND CONTAMINANTS WITH A SPRAY ASSEMBLY; 61/912,959 filed on Dec. 6, 2013 entitled METHOD AND SYSTEM OF MAINTAING A LIQUID LEVEL IN A DISTILLATION TOWER; 61/912,964 filed on Dec. 6, 2013 entitled METHOD AND DEVICE FOR SEPARATING A FEED STREAM USING RADIATION DETECTORS; 61/912,970 filed on Dec. 6, 2013 entitled METHOD AND SYSTEM OF DEHYDRATING A FEED STREAM PROCESSED IN A DISTILLATION TOWER; 61/912,975 filed on Dec. 6, 2013 entitled METHOD AND SYSTEM FOR SEPARATING A FEED STREAM WITH A FEED STREAM DISTRIBUTION MECHANISM; 61/912,978 filed on Dec. 6, 2013 entitled METHOD AND SYSTEM FOR PREVENTING ACCUMULATION OF SOLIDS IN A DISTILLATION TOWER; 61/912,984 filed on Dec. 6, 2013 entitled METHOD AND SYSTEM OF MODIFYING A LIQUID LEVEL DURING START-UP OPERATIONS; 61/912,986 filed on Dec. 6, 2013 entitled METHOD AND DEVICE FOR SEPARATING HYDROCARBONS AND CONTAMINANTS WITH A HEATING MECHANISM TO DESTABILIZE AND/OR PREVENT ADHESION OF SOLIDS; 61/912,987 filed on Dec. 6, 2013 entitled METHOD AND DEVICE FOR SEPARATING HYDROCARBONS AND CONTAMINANTS WITH A SURFACE TREATMENT MECHANISM.

BACKGROUND

Fields of Disclosure

The disclosure relates generally to the field of fluid separation. More specifically, the disclosure relates to the cryogenic separation of contaminants, such as acid gas, from a hydrocarbon.

Description of Related Art

This section is intended to introduce various aspects of the art, which may be associated with the present disclosure. This discussion is intended to provide a framework to facilitate a better understanding of particular aspects of the present disclosure. Accordingly, it should be understood that this section should be read in this light, and not necessarily as admissions of prior art.

The production of natural gas hydrocarbons, such as methane and ethane, from a reservoir oftentimes carries with it the incidental production of non-hydrocarbon gases. Such gases include contaminants, such as at least one of carbon dioxide ("$CO_2$"), hydrogen sulfide ("$H_2S$"), carbonyl sulfide, carbon disulfide and various mercaptans. When a feed stream being produced from a reservoir includes these contaminants mixed with hydrocarbons, the stream is oftentimes referred to as "sour gas."

Many natural gas reservoirs have relatively low percentages of hydrocarbons and relatively high percentages of contaminants. Contaminants may act as a diluent and lower the heat content of the hydrocarbons. Some contaminants, like sulfur-bearing compounds, are noxious and may even be lethal. Additionally, in the presence of water some contaminants can become quite corrosive.

It is desirable to remove contaminants from a stream containing hydrocarbons to produce sweet and concentrated hydrocarbons. Specifications for pipeline quality natural gas typically call for a maximum of 2-4% $CO_2$ and ¼ grain $H_2S$ per 100 scf (4 ppmv) or 5 mg/Nm3 $H_2S$. Specifications for lower temperature processes such as natural gas liquefaction plants or nitrogen rejection units typically require less than 50 ppm $CO_2$.

The separation of contaminants from hydrocarbons is difficult and consequently significant work has been applied to the development of hydrocarbon/contaminant separation methods. These methods can be placed into three general classes: absorption by solvents (physical, chemical and hybrids), adsorption by solids, and distillation.

Separation by distillation of some mixtures can be relatively simple and, as such, is widely used in the natural gas industry. However, distillation of mixtures of natural gas hydrocarbons, primarily methane, and one of the most common contaminants in natural gas, carbon dioxide, can present significant difficulties. Conventional distillation principles and conventional distillation equipment are predicated on the presence of only vapor and liquid phases throughout the distillation tower. The separation of $CO_2$ from methane by distillation involves temperature and pressure conditions that result in solidification of $CO_2$ if a pipeline or better quality hydrocarbon product is desired. The required temperatures are cold temperatures typically referred to as cryogenic temperatures.

Certain cryogenic distillations can overcome the above mentioned difficulties. These cryogenic distillations provide the appropriate mechanism to handle the formation and subsequent melting of solids during the separation of solid-forming contaminants from hydrocarbons. The formation of solid contaminants in equilibrium with vapor-liquid mixtures of hydrocarbons and contaminants at particular conditions of temperature and pressure takes place in a controlled freeze zone section.

Sometimes solids can adhere to an internal (e.g., controlled freeze zone wall) of the controlled freeze zone section rather than melt. Adherence of the solids can result in undesired accumulation of the solids.

The adherence and subsequent accumulation is disadvantageous. The adherence and subsequent accumulation, if uncontrolled, can interfere with the proper operation of the controlled freeze zone and the effective separation of methane from the contaminants.

A need exists for improved technology, including technology that destabilizes and removes any adhesion of solids to surface(s) in the controlled freeze zone section.

SUMMARY

The present disclosure provides a device and method for separating contaminants from hydrocarbons, among other things.

A method of separating in a feed stream in a distillation tower may comprise maintaining a controlled freeze zone section in a distillation tower that operates at a temperature and pressure at which a solid forms; maintaining a melt tray assembly within the controlled freeze zone section that operates at a temperature and pressure at which the solid melts; forming solids in a controlled freeze zone section; raising a liquid level of a liquid in the melt tray assembly when the solids accumulate on a mechanical component in the controlled freeze zone section; raising a liquid temperature of the liquid while raising the liquid level; and lowering the liquid level after at least one of (a) a predetermined time period has passed and (b) an alternative temperature of the mechanical component is within an expected temperature range of a baseline temperature of the mechanical component.

A method of producing a hydrocarbon in a distillation tower may comprise maintaining a controlled freeze zone section in the distillation tower that operates at a temperature and pressure at which a feed stream forms a solid; maintaining a melt tray assembly within the controlled freeze zone section that operates at a temperature and pressure at which the solid melts; forming solids in the controlled freeze zone section; raising a liquid level of a liquid in the melt tray assembly when the solids accumulate on a mechanical component in the controlled freeze zone section; raising a liquid temperature of the liquid while raising the liquid level; lowering the liquid level after at least one of (a) a predetermined time period passed and (b) a detected temperature of the mechanical component is within an expected temperature range of a baseline temperature of the mechanical component; and producing hydrocarbons from the feed stream.

The foregoing has broadly outlined the features of the present disclosure in order that the detailed description that follows may be better understood. Additional features will also be described herein.

BRIEF DESCRIPTION OF THE DRAWINGS

These and other features, aspects and advantages of the disclosure will become apparent from the following description, appending claims and the accompanying drawings, which are briefly described below.

Figure 1:
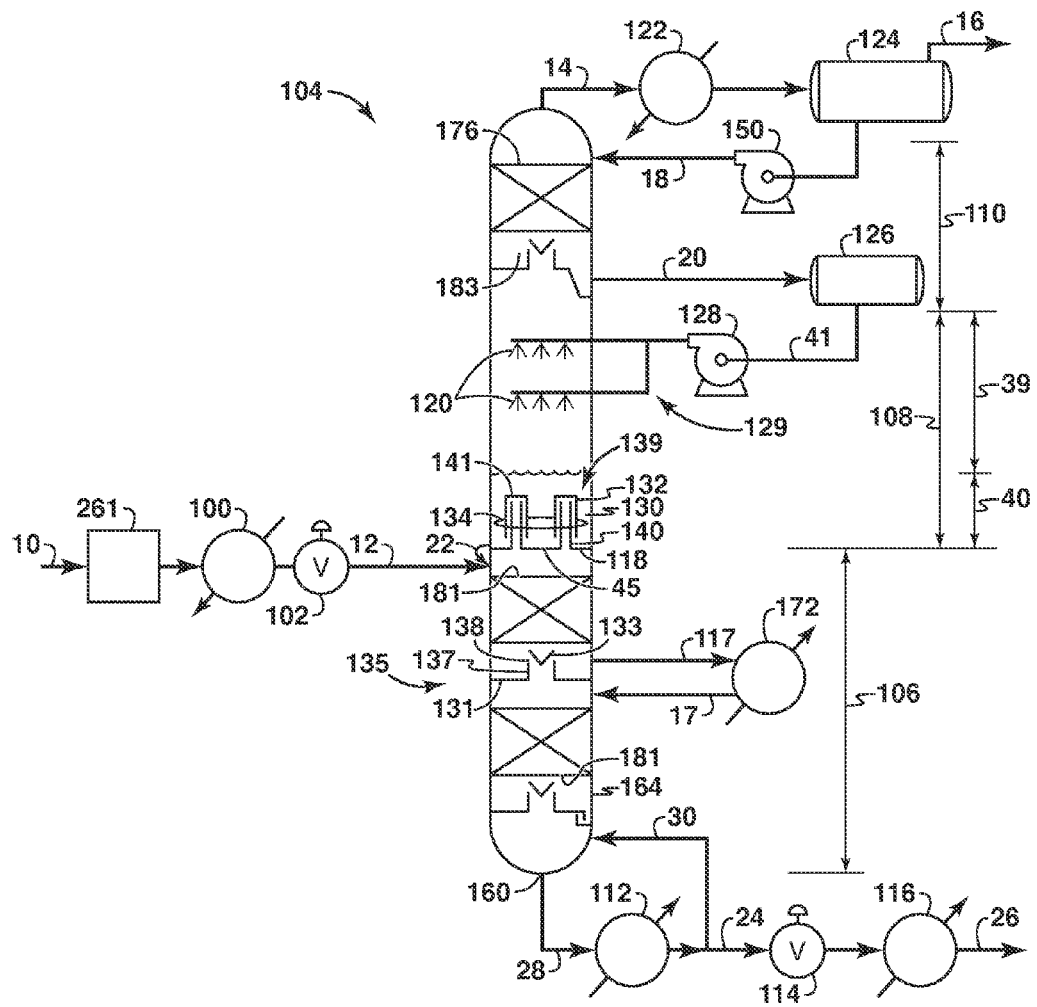
FIG. 1 is a schematic diagram of a tower with sections within a single vessel.

It should be noted that the figures are merely examples and no limitations on the scope of the present disclosure are intended thereby. Further, the figures are generally not drawn to scale, but are drafted for purposes of convenience and clarity in illustrating various aspects of the disclosure.

DETAILED DESCRIPTION

For the purpose of promoting an understanding of the principles of the disclosure, reference will now be made to the features illustrated in the drawings and specific language will be used to describe the same. It will nevertheless be understood that no limitation of the scope of the disclosure is thereby intended. Any alterations and further modifications, and any further applications of the principles of the disclosure as described herein are contemplated as would normally occur to one skilled in the art to which the disclosure relates. It will be apparent to those skilled in the relevant art that some features that are not relevant to the present disclosure may not be shown in the drawings for the sake of clarity.

As referenced in this application, the terms "stream," "gas stream," "vapor stream," and "liquid stream" refer to different stages of a feed stream as the feed stream is processed in a distillation tower that separates methane, the primary hydrocarbon in natural gas, from contaminants. Although the phrases "gas stream," "vapor stream," and "liquid stream," refer to situations where a gas, vapor, and liquid is mainly present in the stream, respectively, there may be other phases also present within the stream. For example, a gas may also be present in a "liquid stream." In some instances, the terms "gas stream" and "vapor stream" may be used interchangeably.

The disclosure relates to a system and method for separating a feed stream in a distillation tower. The system and method helps prevent the accumulation of solids in the controlled freeze zone section by disengaging solids that accumulated in the controlled freeze zone section from the surface(s) where the solids accumulated. The system and method disengages solids by increasing the liquid level of warm liquid in a melt tray assembly of a middle controlled freeze zone section of the distillation tower. The liquid level can be increased to cover at least a portion of the solids so as to cause disengagement of the solids by melting. FIGS. 1-6 of the disclosure display various aspects of the system and method.

Figure 2:
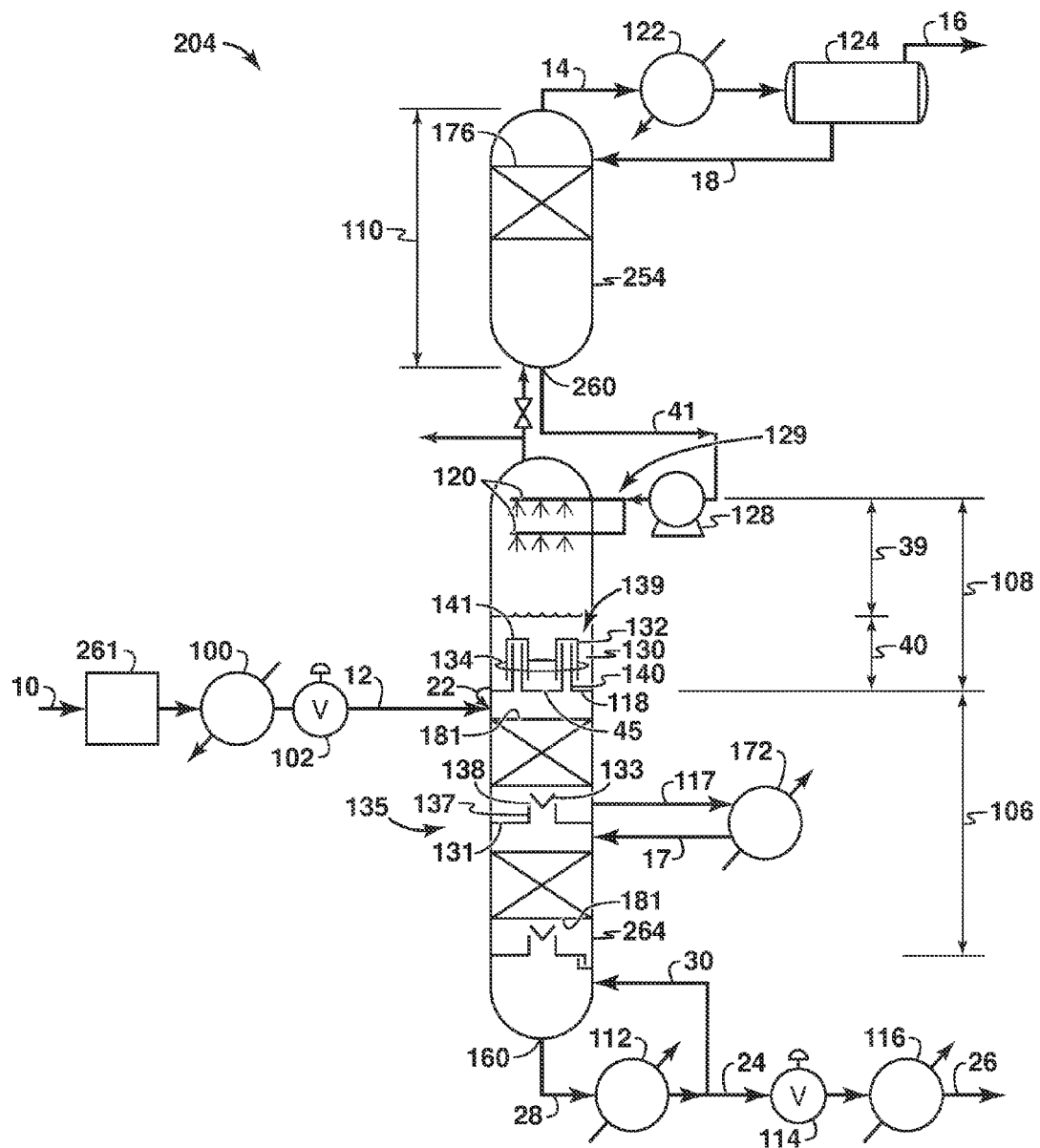
FIG. 2 is a schematic diagram of a tower with sections within multiple vessels.

The system and method may separate a feed stream having methane and contaminants. The system may comprise a distillation tower 104, 204 (FIGS. 1-2). The distillation tower 104, 204 may separate the contaminants from the methane.

The distillation tower 104, 204 may be separated into three functional sections: a lower section 106, a middle controlled freeze zone section 108 and an upper section 110. The distillation tower 104, 204 may incorporate three functional sections when the upper section 110 is needed and/or desired.

The distillation tower 104, 204 may incorporate only two functional sections when the upper section 110 is not needed and/or desired. When the distillation tower does not include an upper section 110, a portion of vapor leaving the middle controlled freeze zone section 108 may be condensed in a condenser 122 and returned as a liquid stream via a spray assembly 129. Moreover, lines 18 and 20 may be eliminated, elements 124 and 126 may be one and the same, and elements 150 and 128 may be one and the same. The stream in line 14, now taking the vapors leaving the middle controlled freeze section 108, directs these vapors to the condenser 122.

The lower section 106 may also be referred to as a stripper section. The middle controlled freeze zone section 108 may also be referred to as a controlled freeze zone section. The upper section 110 may also be referred to as a rectifier section.

Figure 3:
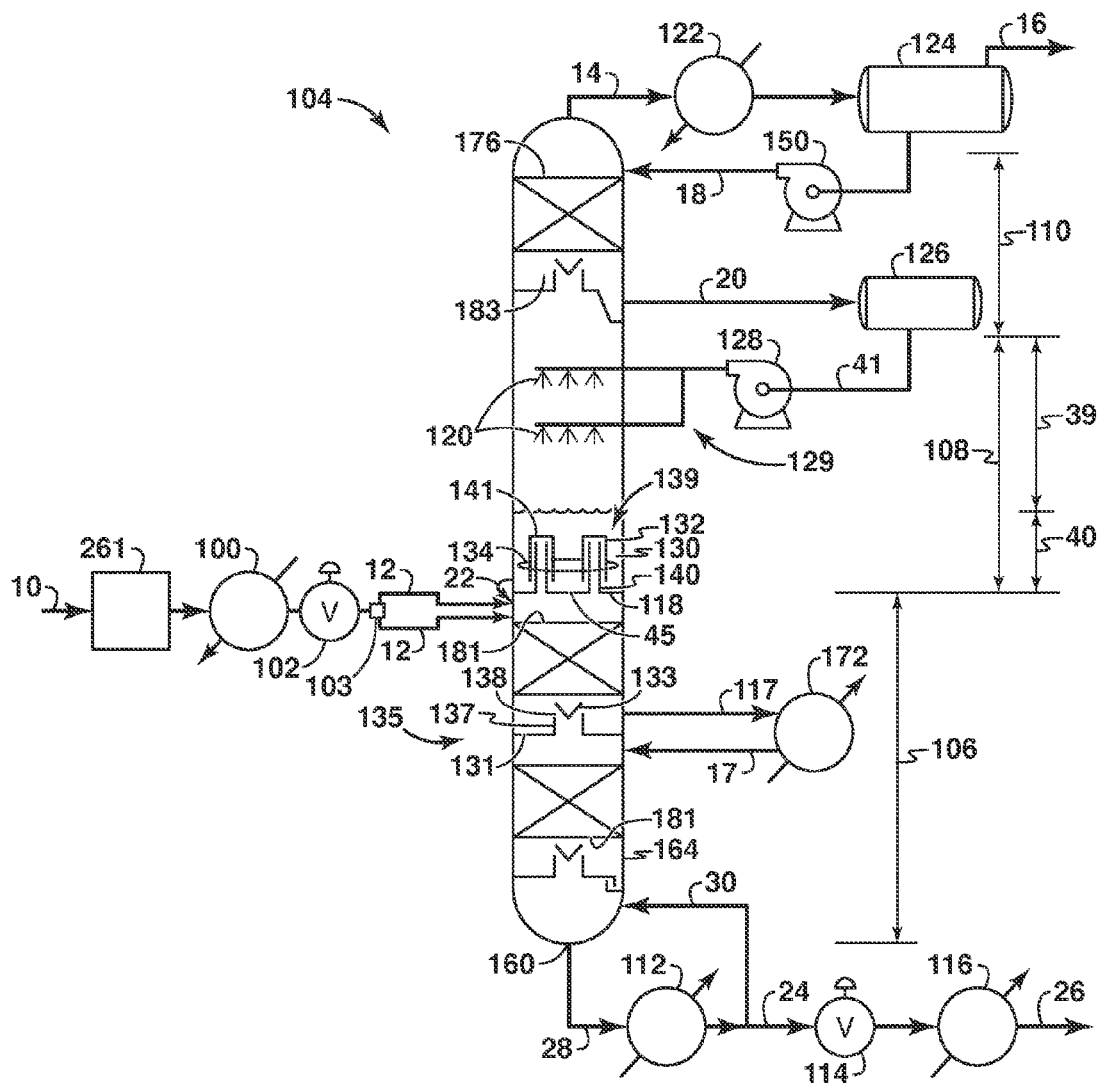
FIG. 3 is a schematic diagram of a tower with sections within a single vessel.

The sections of the distillation tower 104 may be housed within a single vessel (FIGS. 1 and 3). For example, the lower section 106, the middle controlled freeze zone section 108, and the upper section 110 may be housed within a single vessel 164.

Figure 4:
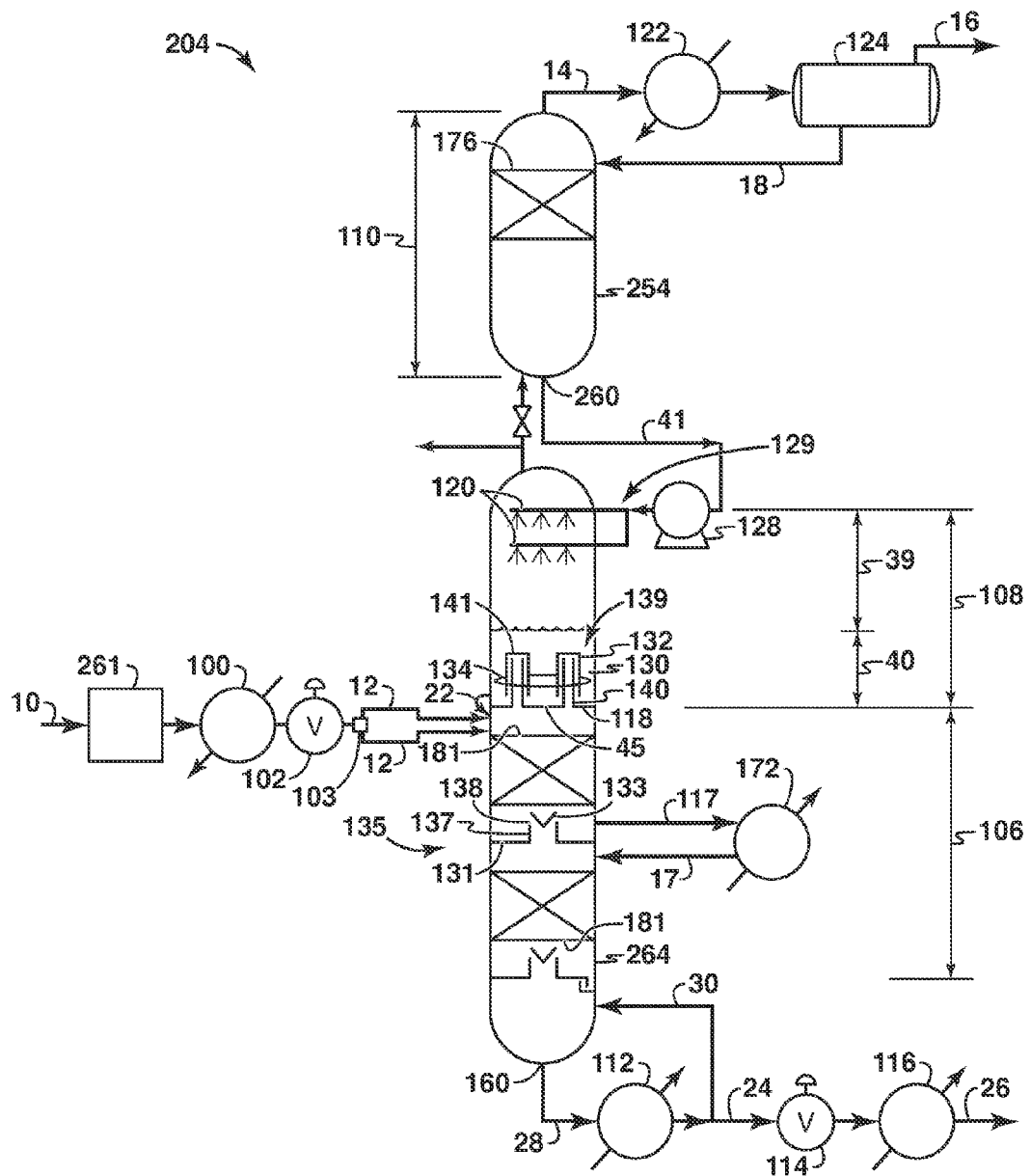
FIG. 4 is a schematic diagram of a tower with sections within multiple vessels.

The sections of the distillation tower 204 may be housed within a plurality of vessels to form a split-tower configuration (FIGS. 2 and 4). Each of the vessels may be separate from the other vessels. Piping and/or another suitable mechanism may connect one vessel to another vessel. In this instance, the lower section 106, middle controlled freeze zone section 108 and upper section 110 may be housed within two or more vessels. For example, as shown in FIGS. 2 and 4, the upper section 110 may be housed within a single vessel 254 and the lower and middle controlled freeze zone sections 106, 108 may be housed within a single vessel 264. When this is the case, a liquid stream exiting the upper section 110, may exit through a liquid outlet bottom 260. The liquid outlet bottom 260 is at the bottom of the upper section 110. Although not shown, each of the sections may be housed within its own separate vessel, or one or more section may be housed within separate vessels, or the upper and middle controlled freeze zone sections may be housed within a single vessel and the lower section may be housed within a single vessel, etc. When sections of the distillation tower are housed within vessels, the vessels may be side-by-side along a horizontal line and/or above each other along a vertical line.

The split-tower configuration may be beneficial in situations where the height of the distillation tower, motion considerations, and/or transportation issues, such as for remote locations, need to be considered. This split-tower configuration allows for the independent operation of one or more sections. For example, when the upper section is housed within a single vessel and the lower and middle controlled freeze zone sections are housed within a single vessel, independent generation of reflux liquids using a substantially contaminant-free, largely hydrocarbon stream from a packed gas pipeline or an adjacent hydrocarbon line, may occur in the upper section. And the reflux may be used to cool the upper section, establish an appropriate temperature profile in the upper section, and/or build up liquid inventory at the bottom of the upper section to serve as an initial source of spray liquids for the middle controlled freeze zone section. Moreover, the middle controlled freeze zone and lower sections may be independently prepared by chilling the feed stream, feeding it to the optimal location be that in the lower section or in the middle controlled freeze zone section, generating liquids for the lower and the middle controlled freeze zone sections, and disposing the vapors off the middle controlled freeze zone section while they are off specification with too high a contaminant content. Also, liquid from the upper section may be intermittently or continuously sprayed, building up liquid level in the bottom of the middle controlled freeze zone section and bringing the contaminant content in the middle controlled freeze zone section down and near steady state level so that the two vessels may be connected to send the vapor stream from the middle controlled freeze zone section to the upper section, continuously spraying liquid from the bottom of the upper section into the middle controlled freeze zone section and stabilizing operations into steady state conditions. The split tower configuration may utilize a sump of the upper section as a liquid receiver for the pump 128, therefore obviating the need for a liquid receiver 126 in FIGS. 1 and 3.

The system may also include a heat exchanger 100 (FIGS. 1-4). The feed stream 10 may enter the heat exchanger 100 before entering the distillation tower 104, 204. The feed stream 10 may be cooled within the heat exchanger 100. The heat exchanger 100 helps drop the temperature of the feed stream 10 to a level suitable for introduction into the distillation tower 104, 204.

The system may include an expander device 102 (FIGS. 1-4). The feed stream 10 may enter the expander device 102 before entering the distillation tower 104, 204. The feed stream 10 may be expanded in the expander device 102 after exiting the heat exchanger 100. The expander device 102 helps drop the temperature of the feed stream 10 to a level suitable for introduction into the distillation tower 104, 204. The expander device 102 may be any suitable device, such as a valve. If the expander device 102 is a valve, the valve may be any suitable valve that may aid in cooling the feed stream 10 before it enters the distillation tower 104, 204. For example, the valve 102 may comprise a Joule-Thompson (J-T) valve.

The system may include a feed separator 103 (FIGS. 3-4). The feed stream may enter the feed separator before entering the distillation tower 104, 204. The feed separator may separate a feed stream having a mixed liquid and vapor stream into a liquid stream and a vapor stream. Lines 12 may extend from the feed separator to the distillation tower 104, 204. One of the lines 12 may receive the vapor stream from the feed separator. Another one of the lines 12 may receive the liquid stream from the feed separator. Each of the lines 12 may extend to the same and/or different sections (i.e. middle controlled freeze zone, and lower sections) of the distillation tower 104, 204. The expander device 102 may or may not be downstream of the feed separator 103. The expander device 102 may comprise a plurality of expander devices 102 such that each line 12 has an expander device 102.

The system may include a dehydration unit 261 (FIGS. 1-4). The feed stream 10 may enter the dehydration unit 261 before entering the distillation tower 104, 204. The feed stream 10 enters the dehydration unit 261 before entering the heat exchanger 100 and/or the expander device 102. The dehydration unit 261 removes water from the feed stream 10 to prevent water from later presenting a problem in the heat exchanger 100, expander device 102, feed separator 103, or distillation tower 104, 204. The water can present a problem by forming a separate water phase (i.e., ice and/or hydrate) that plugs lines, equipment or negatively affects the distillation process. The dehydration unit 261 dehydrates the feed stream to a dew point sufficiently low to ensure a separate water phase does not form at any point downstream during the rest of the process. The dehydration unit may be any suitable dehydration mechanism, such as a molecular sieve or a glycol dehydration unit.

The system may include a filtering unit (not shown). The feed stream 10 may enter the filtering unit before entering the distillation tower 104, 204. The filtering unit may remove undesirable contaminants from the feed stream before the feed stream enters the distillation tower 104, 204. Depending on what contaminants are to be removed, the filtering unit may be before or after the dehydration unit 261 and/or before or after the heat exchanger 100.

The systems may include a line 12 (FIGS. 1-4). The line may also be referred to as an inlet channel 12. The feed stream 10 may be introduced into the distillation tower 104, 204 through the line 12. The line 12 may extend to the lower section 106 or the middle controlled freeze zone section 108 of the distillation tower 104, 204. For example, the line 12 may extend to the lower section 106 such that the feed stream 10 may enter the lower section 106 of the distillation tower 104, 204 (FIGS. 1-4). The line 12 may directly or indirectly extend to the lower section 106 or the middle controlled freeze zone section 108. The line 12 may extend to an outer surface of the distillation tower 104, 204 before entering the distillation tower.

If the system includes the feed separator 103 (FIGS. 3-4), the line 12 may comprise a plurality of lines 12. Each line may be the same line as one of the lines that extends from the feed separator to a specific portion of the distillation tower 104, 204.

The lower section 106 is constructed and arranged to separate the feed stream 10 into an enriched contaminant bottom liquid stream (i.e., liquid stream) and a freezing zone vapor stream (i.e., vapor stream). The lower section 106 separates the feed stream at a temperature and pressure at which no solids form. The liquid stream may comprise a greater quantity of contaminants than of methane. The vapor stream may comprise a greater quantity of methane than of contaminants. In any case, the vapor stream is lighter than the liquid stream. As a result, the vapor stream rises from the lower section 106 and the liquid stream falls to the bottom of the lower section 106.

The lower section 106 may include and/or connect to equipment that separates the feed stream. The equipment may comprise any suitable equipment for separating methane from contaminants, such as one or more packed sections 181, or one or more distillation trays with perforations downcomers and weirs (FIGS. 1-4).

The equipment may include components that apply heat to the stream to form the vapor stream and the liquid stream. For example, the equipment may comprise a first reboiler 112 that applies heat to the stream. The first reboiler 112 may be located outside of the distillation tower 104, 204. The equipment may also comprise a second reboiler 172 that applies heat to the stream. The second reboiler 172 may be located outside of the distillation tower 104, 204. Line 117 may lead from the distillation tower to the second reboiler 172. Line 17 may lead from the second reboiler 172 to the distillation tower. Additional reboilers, set up similarly to the second reboiler described above, may also be used.

The first reboiler 112 may apply heat to the liquid stream that exits the lower section 106 through a liquid outlet 160 of the lower section 106. The liquid stream may travel from the liquid outlet 160 through line 28 to reach the first reboiler 112 (FIGS. 1-4). The amount of heat applied to the liquid stream by the first reboiler 112 can be increased to separate more methane from contaminants. The more heat applied by the reboiler 112 to the stream, the more methane separated from the liquid contaminants, though more contaminants will also be vaporized.

The first reboiler 112 may also apply heat to the stream within the distillation tower 104, 204. Specifically, the heat applied by the first reboiler 112 warms up the lower section 106. This heat travels up the lower section 106 and supplies heat to warm solids entering a melt tray assembly 139 (FIGS. 1-4) of the middle controlled freeze zone section 108 so that the solids form a liquid and/or slurry mix.

The second reboiler 172 applies heat to the stream within the lower section 106. This heat is applied closer to the middle controlled freeze zone section 108 than the heat applied by the first reboiler 112. As a result, the heat applied by the second reboiler 172 reaches the middle controlled freeze zone section 108 faster than the heat applied by the first reboiler 112. The second reboiler 172 also helps with energy integration.

The equipment may include a chimney assembly 135 (FIGS. 1-4). While falling to the bottom of the lower section 106, the liquid stream may encounter one or more of the chimney assemblies 135.

Each chimney assembly 135 includes a chimney tray 131 that collects the liquid stream within the lower section 106. The liquid stream that collects on the chimney tray 131 may be fed to the second reboiler 172. After the liquid stream is heated in the second reboiler 172, the stream may return to the middle controlled freeze zone section 108 to supply heat to the middle controlled freeze zone section 108 and/or the melt tray assembly 139. Unvaporized or partially vaporized stream exiting the second reboiler 172 may be fed back to the distillation tower 104, 204 below the chimney tray 131. Vapor stream exiting the second reboiler 172 may be routed under or above the chimney tray 131 when the vapor stream enters the distillation tower 104, 204.

The chimney tray 131 may include one or more chimneys 137. The chimney 137 serves as a channel that the vapor stream in the lower section 106 traverses. The vapor stream travels through an opening in the chimney tray 131 at the bottom of the chimney 137 to the top of the chimney 137. The opening is closer to the bottom of the lower section 106 than it is to the bottom of the middle controlled freeze zone section 108. The top is closer to the bottom of the middle controlled freeze zone section 108 than it is to the bottom of the lower section 106.

Each chimney 137 has attached to it a chimney cap 133. The chimney cap 133 covers a chimney top opening 138 of the chimney 137. The chimney cap 133 prevents the liquid stream from entering the chimney 137. The vapor stream exits the chimney assembly 135 via the chimney top opening 138.

After falling to the bottom of the lower section 106, the liquid stream exits the distillation tower 104, 204 through the liquid outlet 160. The liquid outlet 160 is within the lower section 106 (FIGS. 1-4). The liquid outlet 160 may be located at the bottom of the lower section 106.

After exiting through the liquid outlet 160, the feed stream may travel via line 28 to the first reboiler 112. The feed stream may be heated by the first reboiler 112 and vapor may then re-enter the lower section 106 through line 30. Unvaporized liquid may continue out of the distillation process via line 24.

The system may include an expander device 114 (FIGS. 1-4). After entering line 24, the heated liquid stream may be expanded in the expander device 114. The expander device 114 may be any suitable device, such as a valve. The valve 114 may be any suitable valve, such as a J-T valve.

The system may include a heat exchanger 116 (FIGS. 1-4). The liquid stream heated by the first reboiler 112 may be cooled or heated by the heat exchanger 116. The heat exchanger 116 may be a direct heat exchanger or an indirect heat exchanger. The heat exchanger 116 may comprise any suitable heat exchanger.

Figure 6:
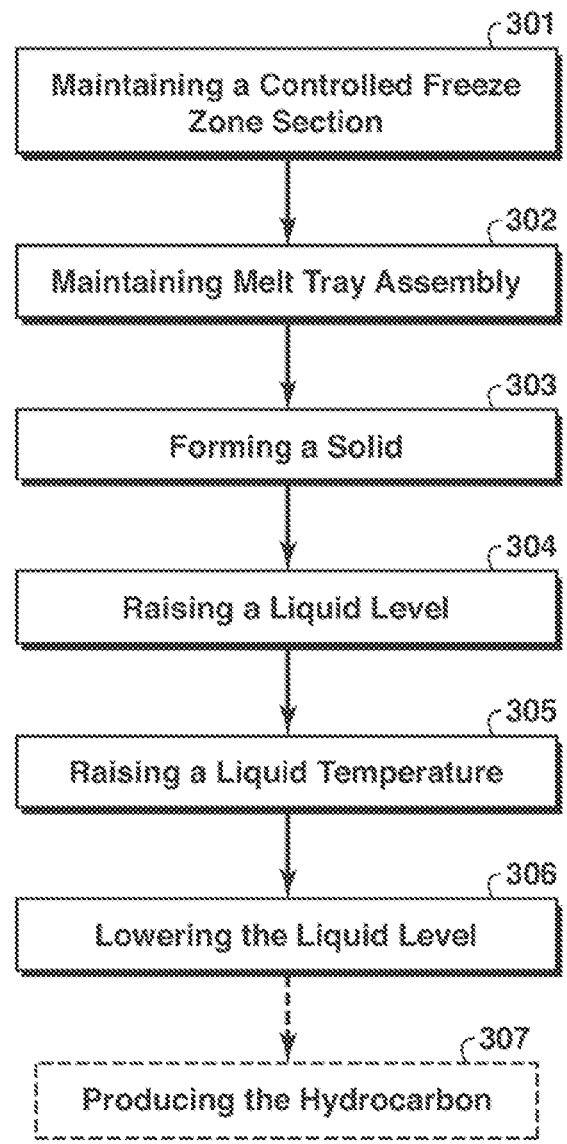
FIG. 6 is a flowchart of a method within the scope of the present disclosure.

The vapor stream in the lower section 106 rises from the lower section 106 to the middle controlled freeze zone section 108. The middle controlled freeze zone section 108 is maintained in the distillation tower 104, 204 to operate at a temperature and pressure at which a solid forms, 301 (FIG. 6). The middle controlled freeze zone section 108 is constructed and arranged to separate the feed stream 10 introduced into the middle controlled freeze zone section, or into the top of lower section 106, into a solid and a vapor stream. The solid may be comprised more of contaminants than of methane. The vapor stream (i.e., methane-enriched vapor stream) may comprise more methane than contaminants.

Figure 5:
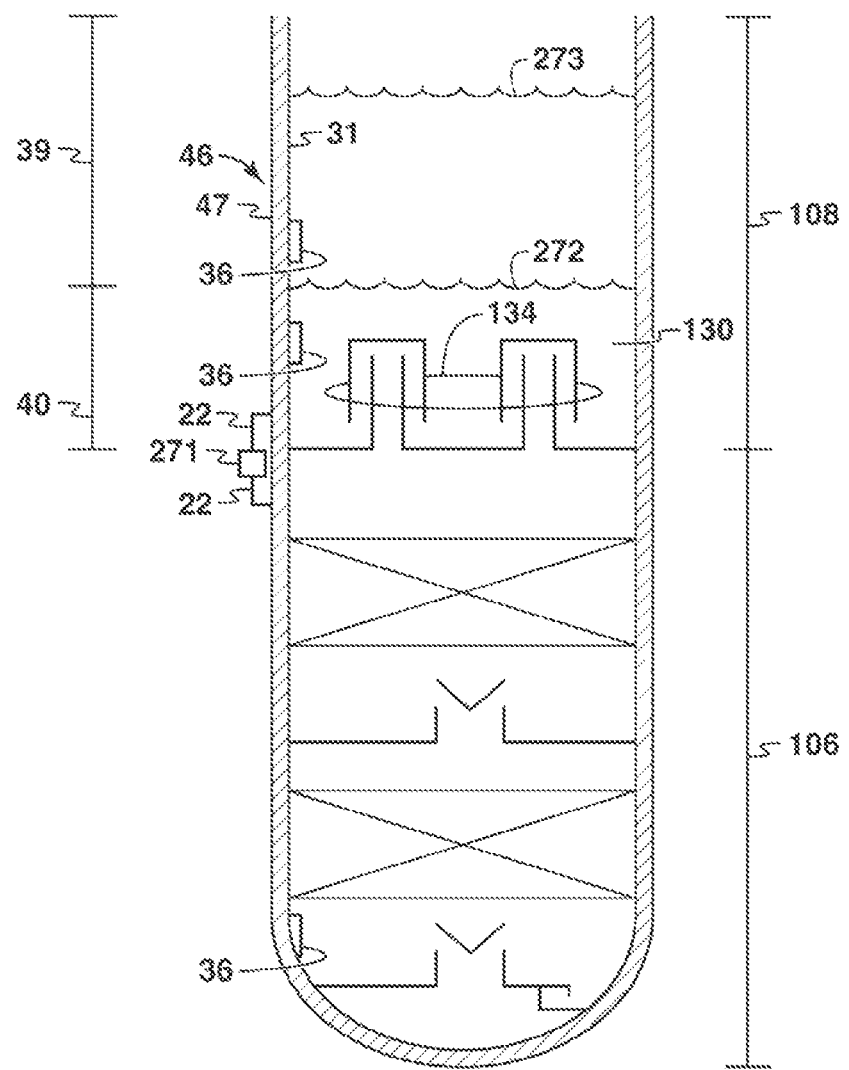
FIG. 5 is a schematic diagram of a portion of a middle controlled freeze zone section and a lower section of a distillation tower showing some of the components of these sections.

The middle controlled freeze zone section 108 includes a lower section 40 and an upper section 39 (FIG. 5). The lower section 40 is below the upper section 39. The lower section 40 directly abuts the upper section 39. The lower section 40 is primarily but not exclusively a heating section of the middle controlled freeze zone section 108. The upper section 39 is primarily but not exclusively a cooling section of the middle controlled freeze zone section 108. The temperature and pressure of the upper section 39 are chosen so that the solid can form in the middle controlled freeze zone section 108.

The middle controlled freeze zone section 108 may comprise a melt tray assembly 139 that is maintained in the middle controlled freeze zone section 108, 302 (FIGS. 1-6). The melt tray assembly 139 is within the lower section 40 of the middle controlled freeze zone section 108. The melt tray assembly 139 is not within the upper section 39 of the middle controlled freeze zone section 108.

The melt tray assembly 139 is constructed and arranged to melt solids formed in the middle controlled freeze zone section 108. When the warm vapor stream rises from the lower section 106 to the middle controlled freeze zone section 108, the vapor stream immediately encounters the melt tray assembly 139 and supplies heat to melt the solid. The melt tray assembly 139 may comprise at least one of a melt tray 118, a bubble cap 132, a liquid 130 and heat mechanism(s) 134.

The melt tray 118 may collect a liquid and/or slurry mix. The melt tray 118 divides at least a portion of the middle controlled freeze zone section 108 from the lower section 106. The melt tray 118 is at the bottom 45 of the middle controlled freeze zone section 108.

One or more bubble caps 132 may act as a channel for the vapor stream rising from the lower section 106 to the middle controlled freeze zone section 108. The bubble cap 132 may provide a path for the vapor stream stream up the riser 140 and then down and around the riser 140 to the melt tray 118. The riser 140 is covered by a cap 141. The cap 141 prevents the liquid 130 from travelling into the riser and it also helps prevent solids from travelling into the riser 140. The vapor stream's traversal through the bubble cap 132 allows the vapor stream to transfer heat to the liquid 130 within the melt tray assembly 139.

One or more heat mechanisms 134 may further heat up the liquid 130 to facilitate melting of the solids into a liquid and/or slurry mix. The heat mechanism(s) 134 may be located anywhere within the melt tray assembly 139. For example, as shown in FIGS. 1-4, a heat mechanism 134 may be located around bubble caps 132. The heat mechanism 134 may be any suitable mechanism, such as a heat coil. The heat source of the heat mechanism 134 may be any suitable heat source.

The liquid 130 in the melt tray assembly is heated by the vapor stream. The liquid 130 may also be heated by the one or more heat mechanisms 134. The liquid 130 helps melt the solids formed in the middle controlled freeze zone section 108 into a liquid and/or slurry mix. Specifically, the heat transferred by the vapor stream heats up the liquid, thereby enabling the heat to melt the solids. The liquid 130 is at a level sufficient to melt the solids.

The middle controlled freeze zone section 108 may also comprise a spray assembly 129. The spray assembly 129 cools the vapor stream that rises from the lower section 40. The spray assembly 129 sprays a liquid spray, which is cooler than the vapor stream, on the vapor stream to cool the vapor stream. The spray assembly 129 is within the upper section 39. The spray assembly 129 is not within the lower section 40. The spray assembly 129 is above the melt tray assembly 139. In other words, the melt tray assembly 139 is below the spray assembly 129.

The spray assembly 129 includes one or more spray nozzles 120 (FIGS. 1-4).

Each spray nozzle 120 sprays liquid spray on the vapor stream. The spray assembly 129 may also include a spray pump 128 (FIGS. 1-4) that pumps the liquid spray. Instead of a spray pump 128, gravity may induce flow in the liquid spray.

The liquid spray sprayed by the spray assembly 129 contacts the vapor stream at a temperature and pressure at which solids form. Solids, containing mainly contaminants, form when the liquid spray contacts the vapor stream. The solids fall toward the melt tray assembly 139.

The temperature in the middle controlled freeze zone section 108 cools down as the vapor stream travels from the bottom of the middle controlled freeze zone section 108 to the top of the middle controlled freeze zone section 108. The methane in the vapor stream rises from the middle controlled freeze zone section 108 to the upper section 110. Some contaminants may remain in the methane and also rise. The contaminants in the vapor stream tend to condense or solidify with the colder temperatures and fall to the bottom of the middle controlled freeze zone section 108.

The solids form the liquid and/or slurry mix when in the liquid 130. The liquid and/or slurry mix flows from the middle controlled freeze zone section 108 to the lower distillation section 106. The liquid and/or slurry mix flows from the bottom of the middle controlled freeze zone section 108 to the top of the lower section 106 via a line 22 (FIGS. 1-4). The line 22 may be an exterior line. The line 22 may extend from the distillation tower 104, 204. The line 22 may extend from the middle controlled freeze zone section 108. The line may extend to the lower section 106. The line 22 may extend from an outer surface of the distillation tower 104, 204.

The vapor stream that rises in the middle controlled freeze zone section 108 and does not form solids or otherwise fall to the bottom of the middle controlled freeze zone section 108, rises to the upper section 110. The upper section 110 operates at a temperature and pressure and contaminant concentration at which no solid forms. The upper section 110 is constructed and arranged to cool the vapor stream to separate the methane from the contaminants. Reflux in the upper section 110 cools the vapor stream. The reflux is introduced into the upper section 110 via line 18. Line 18 may extend to the upper section 110. Line 18 may extend from an outer surface of the distillation tower 104, 204.

After contacting the reflux in the upper section 110, the feed stream forms a vapor stream and a liquid stream. The vapor stream mainly comprises methane. The liquid stream comprises relatively more contaminants. The vapor stream rises in the upper section 110 and the liquid falls to a bottom of the upper section 110.

To facilitate separation of the methane from the contaminants when the stream contacts the reflux, the upper section 110 may include one or more mass transfer devices 176. Each mass transfer device 176 helps separate the methane from the contaminants. Each mass transfer device 176 may comprise any suitable separation device, such as a tray with perforations, or a section of random or structured packing to facilitate contact of the vapor and liquid phases.

After rising, the vapor stream may exit the distillation tower 104, 204 through line 14. The line 14 may emanate from an upper part of the upper section 110. The line 14 may extend from an outer surface of the upper section 110.

From line 14, the vapor stream may enter a condenser 122. The condenser 122 cools the vapor stream to form a cooled stream. The condenser 122 at least partially condenses the stream.

After exiting the condenser 122, the cooled stream may enter a separator 124. The separator 124 separates the vapor stream into liquid and vapor streams. The separator may be any suitable separator that can separate a stream into liquid and vapor streams, such as a reflux drum.

Once separated, the vapor stream may exit the separator 124 as sales product. The sales product may travel through line 16 for subsequent sale to a pipeline and/or condensation to be liquefied natural gas.

Once separated, the liquid stream may return to the upper section 110 through line 18 as the reflux. The reflux may travel to the upper section 110 via any suitable mechanism, such as a reflux pump 150 (FIGS. 1 and 3) or gravity (FIGS. 2 and 4).

The liquid stream (i.e., freezing zone liquid stream) that falls to the bottom of the upper section 110 collects at the bottom of the upper section 110. The liquid may collect on tray 183 (FIGS. 1 and 3) or at the bottommost portion of the upper section 110 (FIGS. 2 and 4). The collected liquid may exit the distillation tower 104, 204 through line 20 (FIGS. 1 and 3) or outlet 260 (FIGS. 2 and 4). The line 20 may emanate from the upper section 110. The line 20 may emanate from a bottom end of the upper section 110. The line 20 may extend from an outer surface of the upper section 110.

The line 20 and/or outlet 260 connect to a line 41. The line 41 leads to the spray assembly 129 in the middle controlled freeze zone section 108. The line 41 emanates from the holding vessel 126. The line 41 may extend to an outer surface of the middle controlled freeze zone section 108.

The line 20 and/or outlet 260 may directly or indirectly (FIGS. 1-4) connect to the line 41. When the line 20 and/or outlet 260 directly connect to the line 41, the liquid spray may be pumped to the spray nozzle(s) 120 via any suitable mechanism, such as the spray pump 128 or gravity. When the line 20 and/or outlet 260 indirectly connect to the line 41, the lines 20, 41 and/or outlet 260 and line 41 may directly connect to a holding vessel 126 (FIGS. 1 and 3). The holding vessel 126 may house at least some of the liquid spray before it is sprayed by the nozzle(s). The liquid spray may be pumped from the holding vessel 126 to the spray nozzle(s) 120 via any suitable mechanism, such as the spray pump 128 (FIGS. 1-2) or gravity. The holding vessel 126 may be needed when there is not a sufficient amount of liquid stream at the bottom of the upper section 110 to feed the spray nozzles 120.

The system may also include one or more temperature sensors 36 (FIG. 5). Each temperature sensor 36 may be coupled to the same and/or a different mechanical component. The temperature sensor 36 detects the temperature of the mechanical component. The mechanical component may be the distillation tower 104, 204 and/or included in the distillation tower 104, 204. For example, to help detect the presence of solids in the middle controlled freeze zone section 108, the mechanical component may be the middle controlled freeze zone section 108 or one or more internals of the middle controlled freeze zone section 108. For example, to detect whether solids have accumulated on a controlled freeze zone wall 46 of the middle controlled freeze zone section 108, the mechanical component may be the controlled freeze zone wall 46. If the mechanical component is the controlled freeze zone wall 46, the mechanical component may be coupled to an internal surface 31 or to an external surface 47 of the controlled freeze zone wall 46 (FIG. 5). The internal surface 31 is the innermost surface of the controlled freeze zone wall 46 and is on an inner surface of the middle controlled freeze zone section 108. The external surface 47 is the outermost surface of the controlled freeze zone wall 46 and is on an outer surface of the middle controlled freeze zone section 108.

Before the distillation tower 104, 204 forms any solids, each temperature sensor 36 detects a baseline temperature of the mechanical component. The baseline temperature is within an expected temperature range. After the distillation tower 104, 204 forms solids, a temperature sensor 36 may detect an alternative temperature. The temperature sensor 36 may detect the alternative temperature a plurality of times and at different intervals in time. The alternative temperature is compared to the expected temperature range to see whether the distillation tower 104, 204 is operating normally. The expected temperature range is a range of temperatures that indicates that the distillation tower 104, 204 is operating normally. Different areas of the distillation tower 104, 204 may have their own expected temperature range that is specific to the nature and purpose of a particular section of the distillation tower 104, 204.

The distillation tower 104, 204 is operating not normally when one or more of a variety of circumstances has occurred. The variety of circumstances may include if solids accumulated on a mechanical component in the middle controlled freeze zone section 108, if the middle controlled freeze zone section 108 is too warm to form solids, if the middle controlled freeze zone section 108 is too cold to melt the solids in the melt tray assembly 139, etc. For example, if the temperature sensor 36 is coupled to the controlled freeze zone external surface 47 within the upper section 39 of the middle controlled freeze zone section 108 then the temperature sensor 36 is expected to detect a fairly cold temperature; that is, close to the actual temperature of liquid spray within the middle controlled freeze zone section 108. If, in this example, the temperature sensor 36 detects a rise in temperature from that expected of the actual temperature of liquid spray, solids have accumulated on the controlled freeze zone wall 46. In other words, if the detected temperature is outside of the expected temperature range by a positive amount, solids have likely accumulated on the controlled freeze zone wall 46. The solids acts as an insulator so solid adhesion is determined when there is an unexpected rise in temperature read by the temperature sensor 36 that is a positive amount outside of the expected temperature range.

If it's determined that the middle controlled freeze zone section 108 is not operating normally because the expected temperature range indicates solids have accumulated on a mechanical component of the middle controlled freeze zone section 108, a liquid level of the liquid 130 in the melt tray assembly 139 may be raised, 304 (FIG. 6). Raising the liquid level includes determining whether solids have accumulated on a mechanical component. The liquid level may be raised from a normal operating level. The normal operating level is the level that the liquid needs to be at to melt solids when the distillation tower 104, 204 is properly functioning. When the liquid level rises, the liquid level goes from a first liquid level 272 to a second liquid level 273 (FIG. 5). The second liquid level is a level where at least a portion of the solids that has accumulated is in contact with the liquid 130.

The liquid 130 may be warmer than the solid and, therefore, may cause at least a portion of the solids in contact with the liquid 130 to detach from whatever surface(s) the solids have accumulated on. The liquid may also cause the solids to melt. Even if the liquid 130 is not in direct contact with all of the accumulated solids, the contact may be sufficient to cause all of the solids to detach by removing enough points or sites of solids adhesion and/or support. If the contact is not sufficient for all of the solids to detach and/or melt, the liquid level can be further modified.

The liquid 130 may be warmer than the normal temperature of the liquid to cause the solids to detach and/or melt more quickly when the liquid level rises. The liquid 130 may be warmer than the normal temperature of the liquid by about 2 to 5 degrees Fahrenheit or 2 to 5 degrees Fahrenheit. To make the liquid 130 warmer than the normal temperature, the temperature of the liquid is raised, 305 (FIG. 6). The temperature of the liquid 130 (i.e., liquid temperature) may be raised by applying heat using at least one of the heat mechanism 134, the first reboiler 112, and the second reboiler 172 utilizing the vapor stream rising from the lower section 106 to the middle controlled freeze zone section 108 as the means to transfer heat from the reboilers to the melt tray. Another means of effectively warming the melt tray would be to by-pass some portion of the feed gas around one or more stages of inlet chilling. This would be particularly applicable to cases where the feed enters the tower just under the melt tray. This would also be a way of quickly adding heat to the melt tray. The first reboiler and second reboiler are each examples of an external heating source that is external to the melt tray assembly 139. Another example of an external heating mechanism is external heat tracing. The heat tracing may be on the external surface 47 of the controlled freeze zone wall 46. The heat tracing may be coupled to the external surface 47. The heat tracing may comprise any suitable electrical heating element that runs along the length of a pipe or tower.

The liquid level may be raised by at least partially closing a flow controlling element 271. The flow controlling element 271 may be located on line 22. When the flow controlling element 271 is at least partially closed, the flow controlling element 271 is closed more than it normally is. During normal operations, the flow controlling element 271 is at least partially open to enable liquid to travel from the melt tray assembly 139 to the lower section 106 for processing. For example, during normal operations the flow controlling element 271 may be greater than 20% open and less than 40% open. During normal operations the flow controlling element 271 can be any percentage within the aforementioned percentages. During normal operations the liquid level may remain substantially constant or constant. When the flow controlling element 271 is closed more than it normally is, the liquid 130 in the melt tray assembly 139 builds up in the melt tray assembly 139, thereby raising a liquid level from the first liquid level 272 to the second liquid level 273. When the flow controlling element 271 is closed more than it normally is, the flow controlling element may be less than or equal to 20% open. The flow controlling element 271 may be any suitable element. For example, the flow controlling element 271 may be a valve.

After being raised, the liquid level may be lowered after at least one of (i) a predetermined time period has passed and (ii) the alternative temperature of the mechanical component is within the expected temperature range of the baseline temperature of the mechanical component, 306 (FIG. 6). The predetermined time period is a period of time that is long enough to allow the liquid in contact with the solids to detach and/or melt the solids. The predetermined time period may be between about 5 to 30 minutes and 5 to 30 minutes.

After at least one of the predetermined time period has passed and the alternative temperature is within an expected temperature range of the baseline temperature, the liquid level may be lowered from the second liquid level 273 to the first liquid level 272. In order to lower the liquid level, the flow controlling element 271 may be opened more than it is when the liquid level is raised. Additionally, the flow controlling element 271 may be opened more than during normal operations so that the liquid level can quickly return to what it is during normal operations. Once the liquid level is back to what it is during normal operations, the flow controlling element 271 may be open as much as it is during normal operations. For example, while trying to get back to the liquid level at normal operations, the flow controlling element may be greater than or equal to about 40% or greater than or equal to 40% open.

Before lowering the liquid level, the temperature of one or more temperature sensors 36 can be detected. The detection determines whether accumulated adherent solids remains. If accumulated solids remain, the temperature of the liquid may be further raised to melt the solids. In addition or alternatively, the liquid level may be further raised. Once the detected temperature helps the determination be made that accumulated solids do not remain, the liquid level may be lowered.

Steady state $CO_2$ material balance calculations could be performed around the system to detect the adhesion of solids in the middle controlled freeze zone section 108. At steady state, the amount of $CO_2$ flowing into the system with the feed stream should substantially equal the sum of i) the amount of $CO_2$ leaving the distillation tower 104, 204 via line 16 and ii) the $CO_2$ leaving the lower section 110 of the distillation tower 104, 204 via the liquid outlet 24. If the amount of $CO_2$ entering the system measurably exceeds the $CO_2$ leaving the system, then $CO_2$ is accumulating in the system, possibly as solids in the middle controlled freeze zone section 108. The amount of $CO_2$ entering the system may be determined by multiplying the feed stream mass flow rate times the $CO_2$ weight percent at the inlet of the distillation tower 104, 204 to obtain a mass $CO_2$ entering/ unit time. The amount of $CO_2$ exiting the distillation tower 104, 204 via line 16 and/or liquid outlet 160 may be determined by multiplying the relevant exiting gas (or liquid) mass flow rates times their respective $CO_2$ weight percent, and summing them to obtain a mass $CO_2$ exiting/ unit time. The difference of $CO_2$ entering minus $CO_2$ exiting represents the instantaneous rate of $CO_2$ mass accumulation (or loss) in the system at that point in time. By collecting a series of these differences and multiplying them by appropriate time increments, it is possible to sum those products together to determine if there is a net gain (or loss) of $CO_2$ in the system over that period. These measurements may be facilitated by the use of Coriolis flow meters, which measure mass flow rates directly and accurately.

Because what would otherwise appear to indicate an accumulation of $CO_2$ in the middle controlled freeze zone section 108 may be due to increasing liquid levels in the middle controlled freeze zone section 108, corrections may be made for changing levels of fluid that contain $CO_2$ (e.g., melt tray assembly liquid level, reboiler liquid level). Appropriate factors may be considered to convert these liquid level changes to mass changes. The mass changes may then be multiplied by their respective $CO_2$ weight percent. If the total apparent $CO_2$ accumulation as calculated by material balance exceeds the $CO_2$ accumulation as measured by changing liquid levels, then solids may be building in the middle controlled freeze zone section 108 of the distillation tower 104, 204.

Persons skilled in the technical field will readily recognize that in practical applications of the disclosed methodology, one or more steps may be performed on a computer, typically a suitably programmed digital computer. Further, some portions of the detailed descriptions which follow are presented in terms of procedures, steps, logic blocks, processing and other symbolic representations of operations on data bits within a computer memory. These descriptions and representations are the means used by those skilled in the data processing arts to most effectively convey the substance of their work to others skilled in the art. In the present application, a procedure, step, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "processing," "computing," "calculating," "detecting," "determining," "displaying," "copying," "producing," "storing," "accumulating," "adding," "applying," "identifying," "consolidating," "waiting," "including," "executing," "maintaining," "updating," "creating," "implementing," "generating," "transforming," or the like, may refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is important to note that the steps depicted in FIG. 6 are provided for illustrative purposes only and a particular step may not be required to perform the inventive methodology. The claims, and only the claims, define the inventive system and methodology.

Aspects of the present disclosure may also relate to an apparatus for performing the operations herein. This apparatus may be specially constructed for the required purposes, or it may comprise a general-purpose computer selectively activated or reconfigured by a computer program stored in the computer. Such a computer program may be stored in a computer readable medium. A computer-readable medium includes any mechanism for storing or transmitting information in a form readable by a machine (e.g., a computer). For example, but not limited to, a computer-readable (e.g., machine-readable) medium includes a machine (e.g., a computer) readable storage medium (e.g., read only memory ("ROM"), random access memory ("RAM"), magnetic disk storage media, optical storage media, flash memory devices, etc.), and a machine (e.g., computer) readable transmission medium (electrical, optical, acoustical or other form of propagated signals (e.g., carrier waves, infrared signals, digital signals, etc.). The computer-readable medium may be non-transitory. The amounts determined may be displayed in the operator's console.

Furthermore, as will be apparent to one of ordinary skill in the relevant art, the modules, features, attributes, methodologies, and other aspects of the disclosure can be implemented as software, hardware, firmware or any combination of the three. Of course, wherever a component of the present disclosure is implemented as software, the component can be implemented as a standalone program, as part of a larger program, as a plurality of separate programs, as a statically or dynamically linked library, as a kernel loadable module, as a device driver, and/or in every and any other way known now or in the future to those of skill in the art of computer programming. Additionally, the present disclosure is in no way limited to implementation in any specific operating system or environment.

Disclosed aspects may be used in hydrocarbon management activities. As used herein, "hydrocarbon management" or "managing hydrocarbons" includes hydrocarbon extraction, hydrocarbon production, hydrocarbon exploration, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities. The term "hydrocarbon management" is also used for the injection or storage of hydrocarbons or $CO_2$, for example the sequestration of $CO_2$, such as reservoir evaluation, development planning, and reservoir management. The disclosed methodologies and techniques may be used to produce hydrocarbons in a feed stream extracted from, for example, a subsurface region. The feed stream extracted may be processed in the distillation tower 104, 204 and separated into hydrocarbons and contaminants. The separated hydrocarbons exit the middle controlled freeze zone section 108 or the upper section 110 of the distillation tower. Some or all of the hydrocarbons that exit are produced, 307. Hydrocarbon extraction may be conducted to remove the feed stream from for example, the subsurface region, which may be accomplished by drilling an oil well using oil well drilling equipment. The equipment and techniques used to drill a well and/or extract the hydrocarbons are well known by those skilled in the relevant art. Other hydrocarbon extraction activities and, more generally, other hydrocarbon management activities, may be performed according to known principles.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numeral ranges provided. Accordingly, these terms should be interpreted as indicating that insubstantial or inconsequential modifications or alterations of the subject matter described are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be understood that numerous changes, modifications, and alternatives to the preceding disclosure can be made without departing from the scope of the disclosure. The preceding description, therefore, is not meant to limit the scope of the disclosure. Rather, the scope of the disclosure is to be determined only by the appended claims and their equivalents. It is also contemplated that structures and features in the present examples can be altered, rearranged, substituted, deleted, duplicated, combined, or added to each other.

The articles "the", "a" and "an" are not necessarily limited to mean only one, but rather are inclusive and open ended so as to include, optionally, multiple such elements.

What is claimed is:

1. A method of separating a feed stream in a distillation tower comprising:
    maintaining a controlled freeze zone section in the distillation tower that operates at a temperature and pressure at which a solid forms;
    maintaining a melt tray assembly within the controlled freeze zone section that operates at a temperature and pressure at which the solid melts;
    forming solids in the controlled freeze zone section;
    raising a liquid level of a liquid in the melt tray assembly when the solids accumulate on a mechanical component in the controlled freeze zone section;
    raising a liquid temperature of the liquid while raising the liquid level; and
    lowering the liquid level after at least one of (a) a predetermined time period has passed and (b) an alternative temperature of the mechanical component is within an expected temperature range of a baseline temperature of the mechanical component.

2. The method of claim 1, wherein raising the liquid level comprises determining whether the solids have accumulated on the mechanical component.

3. The method of claim 1, wherein the mechanical component comprises a controlled freeze zone wall.

4. The method of claim 1, wherein the predetermined time period is about 5 to 30 minutes.

5. The method of claim 1, wherein increasing the liquid temperature comprises applying heat to the liquid with at least one of (i) a heat mechanism included in the melt tray assembly and (ii) an external heating mechanism that is external to the melt tray assembly.

6. The method of claim 5, wherein the heat mechanism comprises a melt coil.

7. The method of claim 5, wherein the external heating mechanism comprises at least one of a first reboiler, a second reboiler and a vapor stream.

8. The method of claim 1, further comprising detecting the baseline temperature before forming the solids in the controlled freeze zone section; and detecting the alternative temperature after forming the solids.

9. The method of claim 8, further comprising repeatedly detecting the alternative temperature and repeatedly determining whether the alternative temperature is within the expected temperature range.

10. A method of producing a hydrocarbon from a feed stream in a distillation tower comprising:
    maintaining a controlled freeze zone section in the distillation tower that operates at a temperature and pressure at which a feed stream forms a solid;
    maintaining a melt tray assembly within the controlled freeze zone section that operates at a temperature and pressure at which the solid melts;
    forming solids in the controlled freeze zone section;
    raising a liquid level of a liquid in the melt tray assembly when the solids accumulate on a mechanical component in the controlled freeze zone section;
    raising a liquid temperature of the liquid while raising the liquid level;
    lowering the liquid level after at least one of (a) a predetermined time period passed and (b) a detected temperature of the mechanical component is within an expected temperature range of a baseline temperature of the mechanical component; and
    producing hydrocarbons from the feed stream.

11. The method of claim 10, wherein raising the liquid level comprises determining whether the solids have accumulated on the mechanical component.

12. The method of claim 10, wherein the mechanical component comprises a controlled freeze zone wall.

13. The method of claim 10, wherein the predetermined time period is about 5 to 30 minutes.

14. The method of claim 10, wherein increasing the liquid temperature comprises applying heat to the liquid with at least one of (i) a heat mechanism included in the melt tray assembly and (ii) an external heating mechanism that is external to the melt tray assembly.

15. The method of claim 14, wherein the heat mechanism comprises a melt coil.

16. The method of claim 14, wherein the external heating mechanism comprises at least one of a first reboiler, a second reboiler, a vapor stream, and a heat tracing.

17. The method of claim 10, further comprising detecting the baseline temperature before forming the solid in the controlled freeze zone section; and detecting the alternative temperature after forming the solids.

18. The method of claim 17, further comprising repeatedly detecting the alternative temperature and repeatedly determining whether the alternative temperature is within the expected temperature range.

* * * * *